US011698338B2

(12) United States Patent
Mori et al.

(10) Patent No.: US 11,698,338 B2
(45) Date of Patent: Jul. 11, 2023

(54) EXHAUST GAS ANALYZER, AND EXHAUST GAS ANALYSIS METHOD

(71) Applicant: HORIBA, LTD., Kyoto (JP)

(72) Inventors: Yuichi Mori, Kyoto (JP); Hirotaka Yabushita, Kyoto (JP)

(73) Assignee: HORIBA, LTD.

( * ) Notice: Subject to any disclaimer, the term of this patent is extended or adjusted under 35 U.S.C. 154(b) by 213 days.

(21) Appl. No.: 16/893,924

(22) Filed: Jun. 5, 2020

(65) Prior Publication Data

US 2020/0386678 A1    Dec. 10, 2020

(30) Foreign Application Priority Data

Jun. 7, 2019    (JP) .................................. 2019-107381

(51) Int. Cl.
*G01N 21/3504*    (2014.01)
*G01N 33/00*    (2006.01)
(Continued)

(52) U.S. Cl.
CPC ..... *G01N 21/3504* (2013.01); *F02D 41/0072* (2013.01); *G01N 33/004* (2013.01); *G01M 15/108* (2013.01); *G01N 2021/3595* (2013.01)

(58) Field of Classification Search
CPC ............. F02D 41/0072; F02D 41/1451; F02D 41/1452; F02D 41/1458; G01M 15/108;
(Continued)

(56) References Cited

U.S. PATENT DOCUMENTS 4,727,849 A * 3/1988 Nishida ............... F02D 41/0052
123/704
4,823,760 A    4/1989 Nishida
(Continued)

FOREIGN PATENT DOCUMENTS

CN    102435440 A    5/2012
JP    63-289266 A    5/1987
(Continued)

OTHER PUBLICATIONS

Office Action dated Apr. 4, 2023 issued in JP patent application No. 2019-107381.

*Primary Examiner* — Tri T Ton
(74) *Attorney, Agent, or Firm* — Brooks Kushman P.C.

(57) ABSTRACT

An exhaust gas analyzer to analyze exhaust gas discharged from an internal combustion engine includes an infrared light source, a photodetector, a $CO_2$ concentration calculation part and an $O_2$ concentration calculation part. The infrared light source irradiates infrared light to the exhaust gas. The photodetector detects infrared light after passing through the exhaust gas. The $CO_2$ concentration calculation part calculates a $CO_2$ concentration in the exhaust gas on the basis of a detection signal obtained by the photodetector. The $O_2$ concentration calculation part calculates an $O_2$ concentration in the exhaust gas from the $CO_2$ concentration by using a fuel combustion reaction equation and an EGR rate in an exhaust gas recirculation system or a value related to the EGR rate.

10 Claims, 5 Drawing Sheets

(51) Int. Cl.
  *F02D 41/00* (2006.01)
  *G01N 21/35* (2014.01)
  *G01M 15/10* (2006.01)

(58) Field of Classification Search
  CPC ....... G01N 2021/3595; G01 21/3504; G01N 33/004; G01N 2201/121; G01N 2201/123; Y02A 50/20
  USPC ................................. 356/432–444, 335–343
  See application file for complete search history.

(56) References Cited

U.S. PATENT DOCUMENTS

2014/0338540 A1* 11/2014 Yoshimura ................ G01F 9/00
  96/413
2020/0063627 A1* 2/2020 Hartland ................... F01N 9/00

FOREIGN PATENT DOCUMENTS

| JP | 63-227948 A | 9/1988 |
| JP | 07-311154 A | 11/1995 |
| JP | 08-062099 A | 3/1996 |
| JP | 10-141147 A | 5/1998 |
| JP | 2000-346801 A | 12/2000 |
| JP | 2008-208723 A | 9/2008 |
| JP | 2009-250935 A | 10/2009 |
| JP | 2012-241569 A | 12/2012 |
| JP | 5196072 B | 5/2013 |
| JP | 2017-142105 A | 8/2017 |
| JP | 2018-021525 A | 2/2018 |

\* cited by examiner

EXHAUST GAS ANALYZER, AND EXHAUST GAS ANALYSIS METHOD

CROSS-REFERENCE TO RELATED APPLICATION

This application claims priority to Japanese Application No. 2019-107381, filed Jun. 7, 2019, the disclosure of which is incorporated in its entirety by reference herein.

BACKGROUND OF THE INVENTION

Field of the Invention

The present invention relates to an exhaust gas analyzer to analyze exhaust gas by using infrared light, and an exhaust gas analysis method.

Background Art

An FTIR analyzer using Fourier transform infrared spectroscopy (FTIR) as described in Patent Document 1 has conventionally been used as one which analyzes components contained in exhaust gas. The FTIR analyzer achieves simultaneous analysis of a plurality of components in the exhaust gas, such as CO, $CO_2$, NO, $H_2O$, $NO_2$, $C_2H_5OH$, HCHO and $CH_4$.

However, the FTIR analyzer is not capable of analyzing a component that does not absorb infrared light even though being capable of analyzing a component that absorbs infrared light. Hence, when measuring a concentration of $O_2$ that does not absorb infrared light, an $O_2$ meter using a magnetic pressure method (PMD) or zirconia method is necessary separately from the FTIR analyzer. Consequently, space to put both the FTIR analyzer and the $O_2$ meter is necessary, resulting in a large-size exhaust gas analyzer.

PRIOR ART DOCUMENT

Patent Document

Patent Document 1: Japanese Unexamined Patent Publication No. 2000-346801

SUMMARY OF THE INVENTION

Problems to be Solved by the Invention

Accordingly, the present invention has been made to solve the above problem, and has for its main object to make it possible to measure an $O_2$ concentration that does not absorb infrared light in an exhaust gas analysis using infrared light.

Means of Solving the Problems

An exhaust gas analyzer in one of embodiments of the present invention is intended to analyze exhaust gas discharged from an internal combustion engine. The exhaust gas analyzer includes an infrared light source, a photodetector, a $CO_2$ concentration calculation part and an $O_2$ concentration calculation part. The infrared light source irradiates infrared light to the exhaust gas. The photodetector detects infrared light after passing through the exhaust gas. The $CO_2$ concentration calculation part calculates a $CO_2$ concentration in the exhaust gas on the basis of a detection signal obtained by the photodetector. The $O_2$ concentration calculation part calculates an $O_2$ concentration in the exhaust gas from the $CO_2$ concentration by using a fuel combustion reaction equation and an EGR rate in an exhaust gas recirculation system or a value related to the EGR rate.

With the exhaust gas analyzer, it is possible to measure the concentration of $O_2$ that does not absorb infrared light without separately disposing an $O_2$ meter because the $O_2$ concentration calculation part calculates the $O_2$ concentration in the exhaust gas by using the fuel combustion reaction equation and the EGR rate in the exhaust gas recirculation system or the value related to the EGR rate. Consequently, the exhaust gas analyzer can be downsized to achieve cost reduction and improved portability. Additionally, the accurate calculation of $O_2$ concentration is achievable because of using not only the fuel combustion reaction equation but also the EGR rate in the exhaust gas recirculation system of the internal combustion engine or the value related to the EGR rate.

The exhaust gas analyzer of the present invention is also capable of analyzing exhaust gas discharged from an internal combustion engine including no exhaust gas recirculation system. In this case, the $O_2$ concentration calculation part calculates an $O_2$ concentration in the exhaust gas from the $CO_2$ concentration by using the fuel combustion reaction equation.

In a conceivable specific embodiment of the $O_2$ concentration calculation part, the $O_2$ concentration calculation part calculates an $O_2$ concentration in the exhaust gas by using a conversion coefficient obtained from a ratio of an $O_2$ coefficient and a $CO_2$ coefficient in the combustion reaction equation, an EGR correction coefficient obtained from the EGR rate or a value related to the EGR rate, and a $CO_2$ concentration variation calculated by the $CO_2$ concentration calculation part.

Examples of the value related to the EGR rate include a concentration of gas returned in the exhaust gas recirculation system, namely, the last $CO_2$ concentration and/or the last $O_2$ concentration, or the last $H_2O$ concentration. As used herein, the last concentration denotes a concentration measured before a predetermined period of time.

The $O_2$ concentration calculation part preferably calculates an $O_2$ concentration in the exhaust gas from the $CO_2$ concentration by using a conversion coefficient determined from the combustion reaction equation, an EGR correction coefficient obtained from the EGR rate or the value related to the EGR rate, and a $CO_2$ concentration variation.

Specifically, the $O_2$ concentration calculation part calculates an $O_2$ concentration according to the following equation:

[$O_2$ concentration]=[Original $O_2$ concentration]–
[Conversion coefficient]×[EGR correction coefficient]×[$CO_2$ concentration variation]

It is conceivable that the $O_2$ concentration calculation part calculates the EGR rate or the value related to EGR rate used for obtaining an EGR correction coefficient in the following manner. Specifically, the $O_2$ concentration calculation part may calculate the EGR rate or the value related to the EGR rate from the $CO_2$ concentration by using a relational expression indicating a relationship between an EGR rate and a $CO_2$ concentration, a relational expression indicating a relationship between an EGR rate, a value related to the EGR rate and a $CO_2$ concentration, or a relational expression indicating a relationship between a value related to an EGR rate and a $CO_2$ concentration.

Individual parameters of the relational expression may be generated by machine learning with the use of training data including a previously acquired EGR rate or a value related to the EGR rate and a $CO_2$ concentration obtained by the $CO_2$ concentration calculation part or other analysis device. For example, individual parameters of a relational expression indicating a relationship between an EGR rate and a $CO_2$ concentration may be generated by machine learning using training data including an EGR rate obtained from outside and a $CO_2$ concentration obtained by the $CO_2$ concentration calculation part or other analysis device.

The exhaust gas analyzer of the present invention may be one which includes a catalyst disposed in an exhaust pipe connecting to the internal combustion engine so as to analyze exhaust gas after passing through the catalyst.

In this case, the $O_2$ concentration calculation part preferably calculates an $O_2$ concentration in the exhaust gas by using a value indicating an oxygen desorption amount or oxygen absorption amount by the catalyst, in addition to the combustion reaction equation and the EGR rate or a value related to the EGR rate.

With the above configuration, it is possible to consider an increase or decrease in $O_2$ concentration due to the catalyst, thus leading to accurate calculation of $O_2$ concentration.

The $O_2$ concentration calculation part preferably calculates an $O_2$ concentration in the exhaust gas by using a conversion coefficient obtained from a ratio of an $O_2$ coefficient and a $CO_2$ coefficient in the combustion reaction equation, an EGR correction coefficient obtained from the EGR rate or a value related to the EGR rate, a catalyst correction coefficient obtained from a value indicating an oxygen desorption amount or oxygen absorption amount by the catalyst, and a $CO_2$ concentration variation calculated by the $CO_2$ concentration calculation part.

Specifically, the $O_2$ concentration calculation part calculates an $O_2$ concentration according to the following equation:

[$O_2$ concentration]=[Original $O_2$ concentration]−
[Conversion coefficient]×[EGR correction coefficient]×[Catalyst correction coefficient]×[$CO_2$ concentration variation]

The $O_2$ concentration calculation part may calculate in the following manner an oxygen desorption amount or oxygen absorption amount by the catalyst used for obtaining a catalyst correction coefficient. Specifically, the $O_2$ concentration calculation part calculates from the $CO_2$ concentration a value indicating an oxygen desorption amount or oxygen absorption amount by the catalyst by using a relational expression indicating a relationship between a value indicating an oxygen desorption amount or oxygen absorption amount by the catalyst and a $CO_2$ concentration.

In order to obtain a high resolution infrared absorption spectrum so as to highly accurately obtain a $CO_2$ concentration, it is preferable to use Fourier transform infrared spectroscopy.

An exhaust gas analysis method in one of embodiments of the present invention is intended to analyze exhaust gas discharged from an internal combustion engine. The method includes calculating a $CO_2$ concentration in the exhaust gas by irradiating infrared light to the exhaust gas, and calculating an $O_2$ concentration in the exhaust gas from the $CO_2$ concentration by using a fuel combustion reaction equation and an EGR rate in an exhaust gas recirculation system or a value related to the EGR rate.

A machine learning apparatus suitably applicable to the exhaust gas analyzer of the present invention is used for irradiating infrared light to exhaust gas discharged from an internal combustion engine so as to detect infrared light after passing through the exhaust gas, and analyzing the exhaust gas on the basis of a detection signal thereof. The machine learning apparatus includes a training data acquisition part to acquire training data including a $CO_2$ concentration and an $O_2$ concentration in the exhaust gas, and a machine learning part to generate pretrained data by performing a machine learning using the training data thus acquired.

An exhaust gas analyzer in one of embodiments of the present invention is intended to analyze exhaust gas discharged from an internal combustion engine. The exhaust gas analyzer includes an infrared light source, a photodetector, a $CO_2$ concentration calculation part and an $O_2$ concentration calculation part. The infrared light source irradiates infrared light to the exhaust gas. The photodetector detects infrared light after passing through the exhaust gas. The $CO_2$ concentration calculation part calculates a $CO_2$ concentration in the exhaust gas on the basis of a detection signal obtained by the photodetector. The $O_2$ concentration calculation part calculates an $O_2$ concentration in the exhaust gas from pretrained data generated by machine learning using training data including a $CO_2$ concentration and an $O_2$ concentration in the exhaust gas, and from a $CO_2$ concentration calculated by the $CO_2$ concentration calculation part.

Effects of the Invention

With the present invention as described above, it is possible to measure the $O_2$ concentration that does not absorb infrared light in the exhaust gas analysis using infrared light.

DESCRIPTION OF THE EMBODIMENTS

An exhaust gas analyzer in one of embodiments of the present invention is described below with reference to the drawings.

Figure 1:
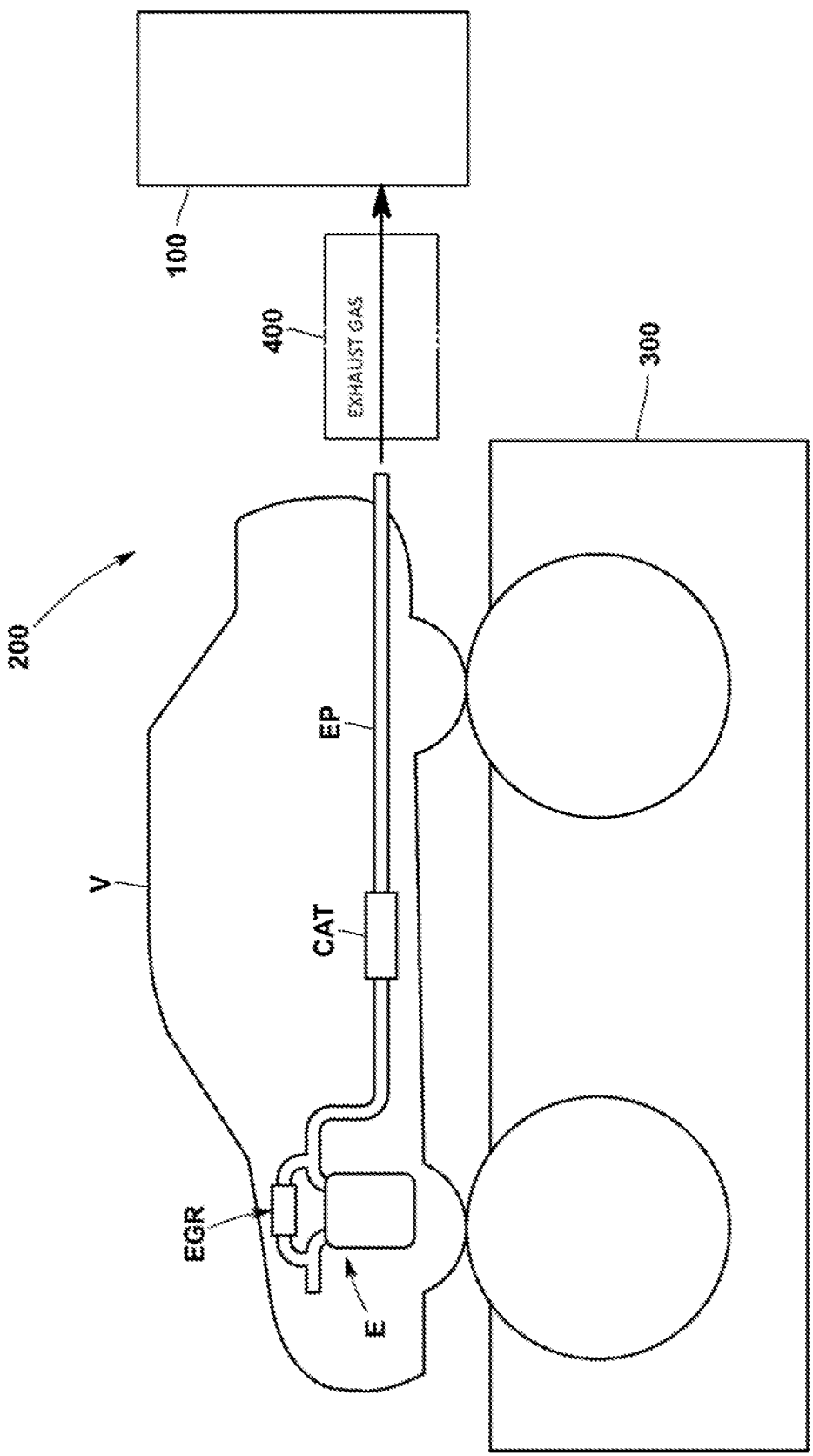
FIG. 1 is a general schematic diagram of an exhaust gas measurement system in one of embodiments of the present invention.

The exhaust gas analyzer 100 in the present embodiment constitutes a part of, for example, an exhaust gas measurement system 200. As illustrated in FIG. 1, the exhaust gas measurement system 200 includes a chassis dynamometer 300, an exhaust gas sampling device 400 to directly sample, without diluting, exhaust gas from a test vehicle V as a specimen that runs on the chassis dynamometer 300, and the exhaust gas analyzer 100 to analyze a measurement target component in the sampled exhaust gas. The test vehicle V as the specimen includes an internal combustion engine F including an exhaust gas recirculation (EGR) system.

Figure 2:
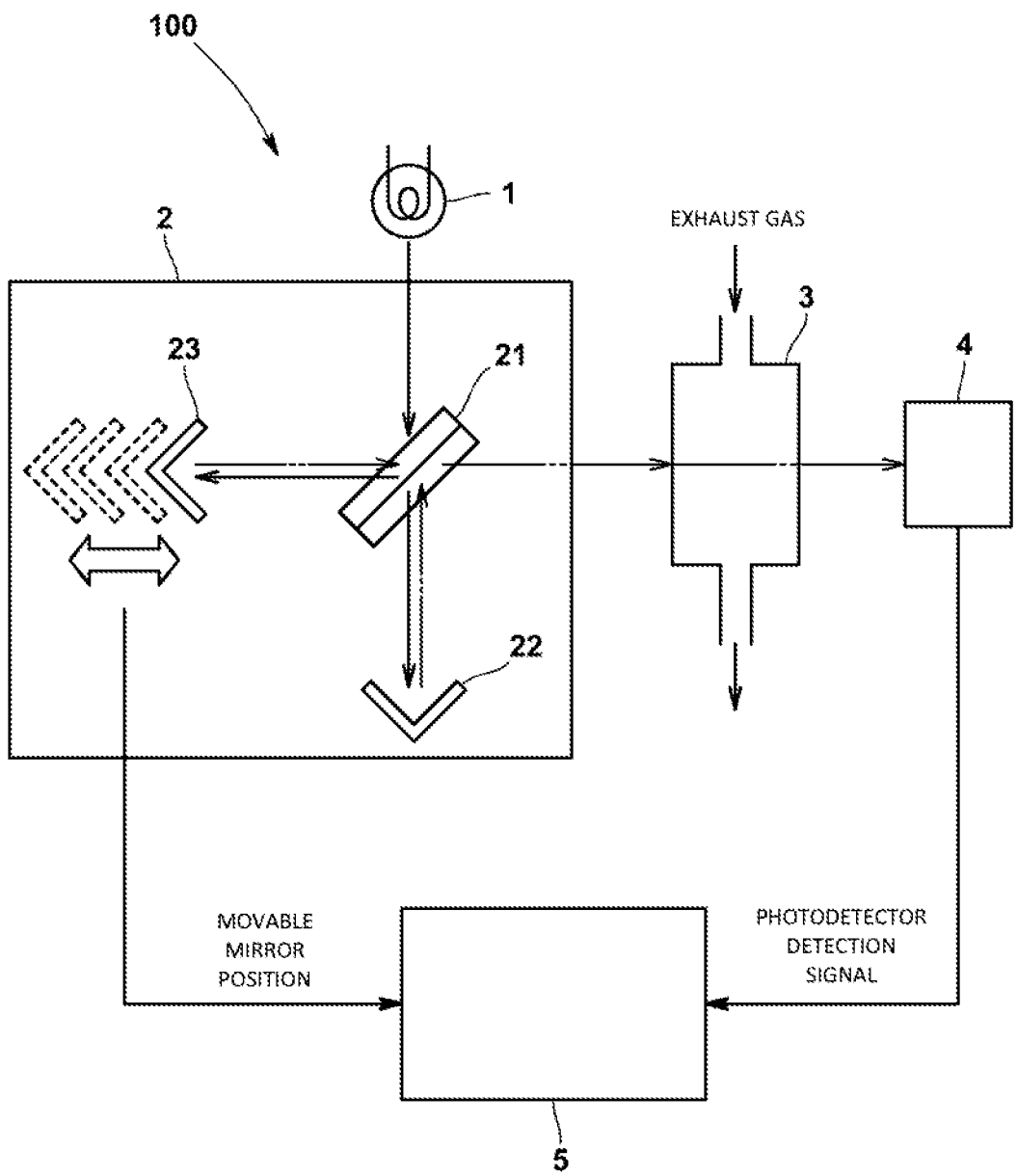
FIG. 2 is a schematic diagram illustrating a configuration of an exhaust gas analyzer in the embodiment.

Specifically, the exhaust gas analyzer 100 is an analyzer using the Fourier transform infrared spectroscopy (FTIR) including an infrared light source 1, an interferometer (spectral part) 2, a measurement cell 3, a photodetector 4 and an arithmetic processing part 5 as illustrated in FIG. 2.

The infrared light source 1 irradiates infrared light having a broad spectrum (continuous light including lights of a large number of wavenumbers). For example, a tungsten halogen lamp or high-brightness ceramic light source is used as the infrared light source 1.

The interferometer 2 is one which uses a so-called Michelson interferometer including a half mirror (beam splitter) 21, a stationary mirror 22 and a movable mirror 23 as illustrated in FIG. 2. Infrared light from the infrared light source 1 which has entered the interferometer 2 is divided into reflected light and transmitted light by the half mirror 21. One of the lights is reflected by the stationary mirror 22, and the other is reflected by the movable mirror 23. Both return to the half mirror 21 and are combined and output from the interferometer 2.

The measurement cell 3 is a transparent cell that permits introduction of sampled exhaust gas. It is configured so that light output from the interferometer 2 passes through the exhaust gas in the measurement cell 3 into the photodetector 4.

The photodetector 4 detects infrared light after passing through the exhaust gas and outputs a detection signal (light intensity signal) thereof to the arithmetic processing part 5. The photodetector 4 is an MCT (Hg CdTe) detector in the present embodiment, but may be a photodetector including other infrared detection element.

The arithmetic processing part 5 includes, for example, an analog electric circuit including a buffer, an amplifier or the like, a digital electric circuit including a CPU, memory, DSP or the like, and an A/D converter disposed between these two circuits.

Figure 3:
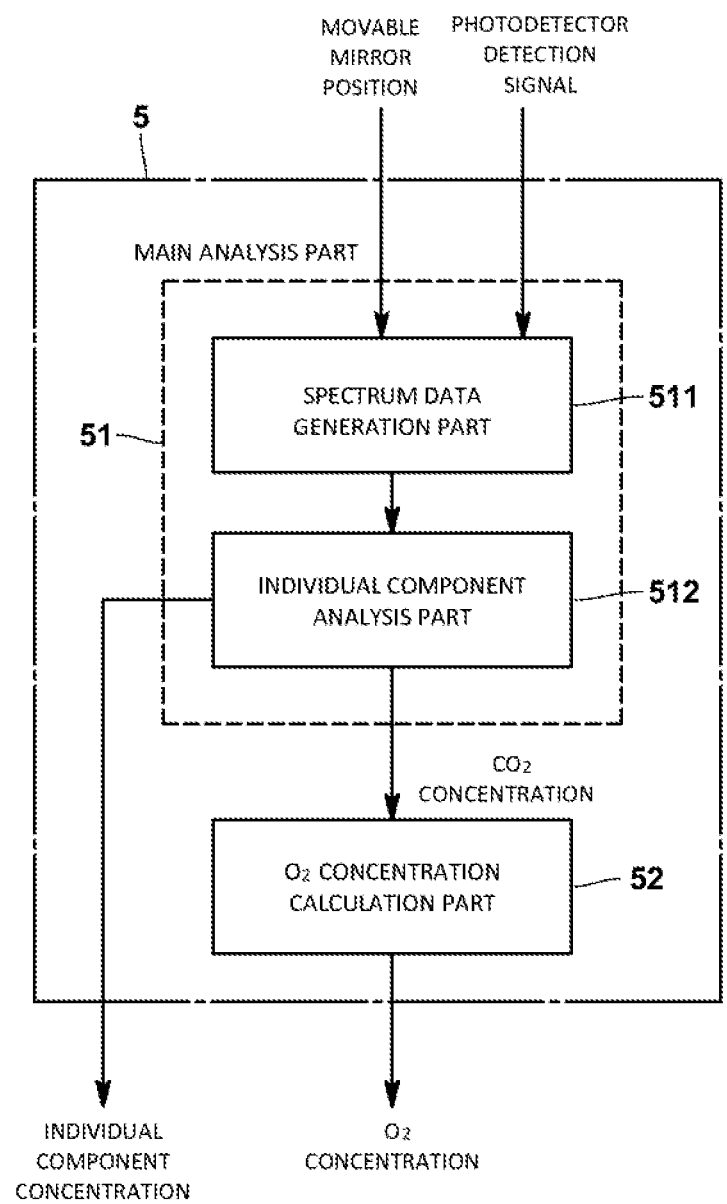
FIG. 3 is a functional block diagram of an arithmetic processing part in the embodiment.

The arithmetic processing part 5 calculates transmitted light spectrum data indicating a spectrum of the light transmitted through a sample from the detection signal obtained by the photodetector 4 as illustrated in FIG. 3, by cooperation between the CPU and peripheral devices thereof according to a predetermined program stored in the memory. The arithmetic processing part 5 calculates infrared absorption spectrum data from the transmitted light spectrum data, thereby determining various components in the exhaust gas. The arithmetic processing part 5 also performs a function as a main analysis part 51 to calculate concentrations of the individual components.

The main analysis part 51 includes a spectrum data generation part 511 and an individual component analysis part 512 that serves as a $CO_2$ concentration calculation part.

If intensity of the light after passing through the exhaust gas is observed by moving forward and backward the movable mirror 23, whose position is set on a horizontal axis, light intensity draws a sine curve due to interference in the case of light of a single wave number. Actual light after passing through the exhaust gas is continuous light, and the sine curve differs depending on wave number. Therefore, actual light intensity corresponds to overlapping of sine curves drawn by individual wave numbers, and an interference pattern (interferogram) has a wave flux shape.

In the spectrum data generation part 511, the position of the movable mirror 23 is found by, for example, a range finder (not illustrated), such as an HeNe laser (not illustrated), and light intensity at individual positions of the movable mirror 23 is found by the photodetector 4. An interference pattern obtainable from these is subjected to Fast Fourier transform (FFT), thereby transforming to transmitted spectrum data whose horizontal axis is individual wave number. Then, for example, on the basis of transmitted light spectrum data obtained by previously measuring in a state in which a measurement cell is empty, the transmitted light spectrum data of the exhaust gas is further transformed to infrared absorption spectrum data.

The individual component analysis part 512 determines various components (for example, CO, $CO_2$, NO, $H_2O$ and $NO_2$) contained in a measurement sample from, for example, individual peak positions (wave numbers) and their heights of the infrared absorption spectrum data, and also calculates concentrations of individual components.

Thus, with the present embodiment, the arithmetic processing part 5 serves as, for example, an $O_2$ concentration calculation part 52 in order to achieve calculation of a concentration of $O_2$ in the exhaust gas that does not absorb infrared light.

The $O_2$ concentration calculation part 52 calculates an $O_2$ concentration in the exhaust gas from a $CO_2$ concentration obtained by the individual component analysis part 512 that is the $CO_2$ concentration calculation part by using a fuel combustion reaction equation. The fuel combustion reaction equation indicates a relationship between $CO_2$ and $H_2O$ generated during the fuel combustion.

The $O_2$ concentration calculation part 52 calculates the $O_2$ concentration in the exhaust gas on the basis of the following prerequisites.
(1) Hydrocarbon (CxHy) that is fuel is completely burned (incomplete burning is ignored, and $O_2$ generated by CO generation reaction is negligibly small).
(2) Amounts of generation of NOx and SOx are small ($O_2$ consumed by a reaction for generating them is negligibly small).
(3) O component, such as alcohol, included in the fuel is negligibly small.
(4) X and y in hydrocarbon (CxHy) being the fuel are kept constant (Actually, a weighted average value based on a volume of an individual hydrocarbon is kept constant).

The $O_2$ concentration calculation part 52 is capable of calculating an $O_2$ concentration from a $CO_2$ concentration by using the following combustion reaction equation.

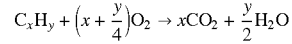

Specifically the $O_2$ concentration calculation part 52 calculates an $O_2$ concentration from a $CO_2$ concentration by using the following conversion equation.

[$O_2$ concentration]=[Original $O_2$ concentration]–
[Conversion coefficient]×[$CO_2$ concentration variation]

As used herein, [original $O_2$ concentration] is an $O_2$ concentration in air sucked into an engine (an initial concentration before reaction, for example, 20.7%).

[$CO_2$ concentration variation] equals to [$CO_2$ concentration generated by combustion reaction]–
[$CO_2$ concentration in air before reaction].

In the present embodiment, [$CO_2$ concentration in air before reaction] is approximately 390 ppm and extremely smaller than [$CO_2$ concentration generated by combustion reaction]. Therefore, [$CO_2$ concentration variation] is [$CO_2$ concentration generated by combustion reaction], namely, the $CO_2$ concentration obtained by the individual component analysis part 512 that is the $CO_2$ concentration calculation part.

[Conversion coefficient] indicates a ratio of $O_2$ consumed and $CO_2$ generated in a complete combustion reaction, and is obtainable from a coefficient (x+y/4) of $O_2$ and a coefficient x of $CO_2$ in the complete combustion reaction equation. For example, the [conversion coefficient] of gasoline is approximately 1.5. In other words, [conversion coefficient]×[$CO_2$ concentration variation] in the conversion equation indicates a change in $O_2$ concentration occurred in the complete combustion reaction.

Alternatively, the $O_2$ concentration calculation part 52 may be configured to calculate an $O_2$ concentration by using the following conversion equation taking an $H_2O$ concentration into consideration. This makes it possible to consider a change of a total number of moles in the combustion reaction equation, thereby improving accuracy of $O_2$ concentration.

[$O_2$ concentration]=[Original $O_2$ concentration]−[Conversion coefficient 1]×[$CO_2$ concentration variation]−[Conversion coefficient 2]×[$H_2O$ concentration variation]

Similar to the above-mentioned [conversion coefficient], [conversion coefficient 1] indicates a ratio of $O_2$ consumed and $CO_2$ generated in a complete combustion reaction, and is obtainable from a coefficient of $O_2$ (x+y/4) and a coefficient x of $CO_2$ in the complete combustion reaction equation.

[Conversion coefficient 2] indicates a ratio of $O_2$ consumed and $H_2O$ generated in a complete combustion reaction, and is obtainable from a coefficient of $O_2$ (x+y/4) and a coefficient y/2 of $H_2O$ in the complete combustion reaction equation.

The above conversion equation focuses only on a combustion reaction equation. An actual internal combustion engine E may include an exhaust gas recirculation (EGR) system in some cases. A catalyst (CAT), such as three-way catalyst, is disposed in an exhaust pipe EP connecting to the internal combustion engine E.

For this purpose, the $O_2$ concentration calculation part 52 includes a function to calculate an $O_2$ concentration taking into consideration an EGR model indicating an operation state of the exhaust gas recirculation (EGR) system, and a function to calculate an $O_2$ concentration taking into consideration a catalyst model indicating a catalytic reaction of the catalyst (CAT).

On the calculation of the $O_2$ concentration taking the EGR model into consideration, the $O_2$ concentration calculation part 52 calculates the $O_2$ concentration from the $CO_2$ concentration by using the following conversion equation.

[$O_2$ concentration]=[Original $O_2$ concentration]−[Conversion coefficient]×[EGR correction coefficient]×[$CO_2$ concentration variation]

As used herein, [EGR correction coefficient] is a coefficient determined by the EGR model, and employs an EGR rate as a parameter.

The [EGR correction coefficient] is obtainable from a relational expression indicating a relationship between an EGR rate and a $CO_2$ concentration in present embodiment.

The relational expression of EGR rate is obtainable by approximating, with least squares method, a relationship between an EGR rate obtained from a $CO_2$ concentration on a intake side and a $CO_2$ concentration on an exhaust side, and a $CO_2$ concentration obtained by the $CO_2$ calculation part (individual component analysis part 512). Alternatively, the relational expression may be set by using, for example, a sigmoid function. Still alternatively, individual parameters in the relational expression are obtainable by machine learning with the use of training data including an EGR rate acquired from outside and a $CO_2$ concentration obtained by the $CO_2$ calculation part (individual component analysis part 512).

The $O_2$ concentration calculation part 52 may be configured to more accurately estimate an $O_2$ concentration by applying a function f whose parameters are, for example, a last $O_2$ concentration and a last $CO_2$ concentration, in addition to [EGR correction coefficient].

[$O_2$ concentration]=[Original $O_2$ concentration]−[Conversion coefficient]×[EGR correction coefficient]×[$CO_2$ concentration variation]+f (last $CO_2$ concentration, last $O_2$ concentration, last $H_2O$ concentration, EGR rate r).

As used herein, the function f can be simply expressed, for example, by r×[EGR correction coefficient 2]×[Last $O_2$ concentration]+r×[EGR correction coefficient 3]×[Last $CO_2$ concentration]+r×[EGR correction coefficient 4]×[Last $H_2O$ concentration]. The term "last" denotes, for example, less than 1 second.

On the calculation of the $O_2$ concentration taking the catalyst model into consideration, the $O_2$ concentration calculation part 52 calculates an $O_2$ concentration from a $CO_2$ concentration by using the following conversion equation.

[$O_2$ concentration]=[Original $O_2$ concentration]−[Conversion coefficient]×[Catalyst correction coefficient]×[$CO_2$ concentration variation]

As used herein, [catalyst correction coefficient] is a coefficient determined by a catalyst model. This may be a correction coefficient that corrects both an oxygen desorption amount and oxygen absorption amount achieved by the catalyst, or may be an individual correction coefficient that individually corrects an oxygen desorption amount and an oxygen absorption amount achieved by the catalyst.

In the case of the individual correction coefficient, a calculation can be made in the following manner.

A correction coefficient to correct the oxygen desorption amount by the catalyst is obtained from a value indicating an oxygen desorption amount by the catalyst, which is obtained from a relational expression indicating a relationship between a value indicating an oxygen desorption amount by the catalyst and a $CO_2$ concentration. The value indicating the oxygen desorption amount by the catalyst is, for example, a proportion of reaction with $O_2$ in a gas phase in the catalyst.

A relational expression of the desorption amount can be obtained by experimentally obtaining a relationship between a proportion of reaction with $O_2$ in the gas phase in the catalyst (that is, a proportion of $O_2$ in the gas, not O2 supplied from the oxygen source stored in the catalyst, out of oxygen consumed in combustion reaction) and the $CO_2$ concentration obtained by the $CO_2$ concentration calculation part (the individual component analysis part 512), and by approximating the relationship with least-squares method or the like. Alternatively, the relational expression may be set by using, for example, a sigmoid function. Still alternatively, individual coefficients of the relational expression are obtainable by machine learning with the use of training data including a reaction proportion acquired from outside and a $CO_2$ concentration obtained by the $CO_2$ calculation part (individual component analysis part 512). Besides the above, the relational expression may be a function whose parameter is an $O_2$ concentration. In this case, it is conceivable to solve the entire conversion equation in terms of [$O_2$ concentration] and remove [$O_2$ concentration] from a right hand side.

A correction coefficient taking into consideration an oxygen absorption amount by the catalyst which is obtained from a value indicating an oxygen absorption amount by the catalyst obtained from a relational expression indicating a relationship between a value indicating an oxygen absorption amount by the catalyst and a $CO_2$ concentration. The value indicating the oxygen absorption amount by the catalyst is, for example, a proportion of a defect site on catalyst capable of taking in oxygen.

A relational expression of the absorption amount can be obtained by experimentally obtaining a relationship between the proportion of the defect site on the catalyst capable of taking in oxygen and the $CO_2$ concentration obtained by the $CO_2$ concentration calculation part (the individual component analysis part 512), and by approximating the relationship with least-squares method or the like. Alternatively, the relational expression may be set by using, for example, a sigmoid function. Still alternatively, individual parameters of the relational expression are obtainable by machine learning with the use of training data including a proportion of the defect site on the catalyst acquired from outside and a $CO_2$ concentration obtained by the $CO_2$ calculation part (individual component analysis part 512). Besides the above, the relational expression may be a function whose parameter is an $O_2$ concentration. In this case, it is conceivable to solve the entire conversion equation in terms of [$O_2$ concentration] and remove [an $O_2$ concentration] from a right hand side.

Although the $O_2$ concentration calculation part 52 has been described above as one which is configured to individually calculate the $O_2$ concentration taking the EGR model into consideration and the $O_2$ concentration taking the catalyst model into consideration, the $O_2$ concentration calculation part 52 may be configured to calculate an $O_2$ concentration taking both the EGR model and the catalyst model into consideration.

On the calculation of the $O_2$ concentration taking both the EGR model and the catalyst model into consideration, the $O_2$ concentration calculation part 52 calculates an $O_2$ concentration from a $CO_2$ concentration by using the following conversion equation.

[$O_2$ concentration]=[Original $O_2$ Concentration]−
[Conversion coefficient]×[EGR correction coefficient]×[Catalyst correction coefficient]×[$CO_2$ concentration variation]

Effects of Present Embodiment

With the exhaust gas analyzer 100 in the present embodiment thus configured, the $O_2$ concentration calculation part 52 calculates the $O_2$ concentration in the exhaust gas by using the fuel combustion reaction equation and the EGR model indicating the operation state of the exhaust gas recirculation (EGR) system. It is therefore possible to measure the concentration of $O_2$ that does not absorb infrared light without separately disposing an $O_2$ meter. Consequently, the exhaust gas analyzer 100 can be downsized to achieve cost reduction and improved portability. Additionally, the accurate calculation of $O_2$ concentration is achievable because of using the EGR model indicating the operation state of the exhaust gas recirculation (EGR) system of the internal combustion engine E.

Other Modified Embodiments

The present invention is not limited to the above embodiments.

For example, with the above embodiment, [EGR correction coefficient] and [catalyst correction coefficient] are obtained separately from [conversion coefficient]. Alternatively, [conversion coefficient] and [EGR correction coefficient] may be combined into one coefficient. Still alternatively, [conversion coefficient]. [EGR correction coefficient] and [catalyst correction coefficient] may be combined into one coefficient.

The $O_2$ concentration calculation part 52 in the present embodiment may be configured to be switchable among an $O_2$ concentration calculation function taking only a combustion reaction equation into consideration, an $O_2$ concentration calculation function taking an EGR model into consideration, an $O_2$ concentration calculation function taking a catalyst model into consideration, and an $O_2$ concentration calculation function taking an EGR model and a catalyst model into consideration. With this embodiment, switching may be carried out through input of a switch signal by a user. Alternatively the individual calculation functions may be switched on the basis of, for example, a component concentration of a $CO_2$ concentration obtained by the individual component analysis part 512.

Figure 4:
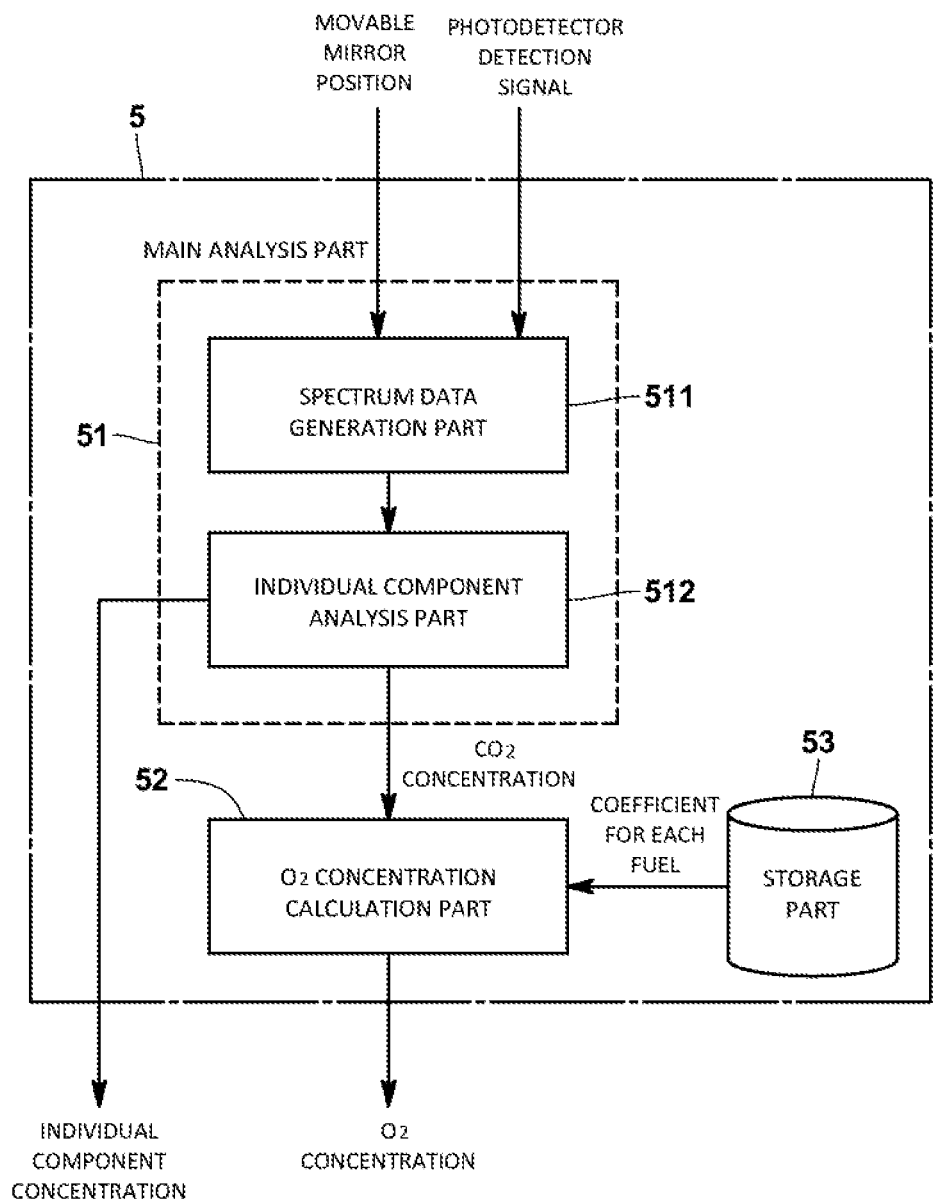
FIG. 4 is a functional block diagram of an arithmetic processing part in a modified embodiment.

As illustrated in FIG. 4, the arithmetic processing part 5 includes a storage part 53 to store [a conversion coefficient], [an EGR correction coefficient] or [a catalyst correction coefficient] for each kind of fuel. Depending on the kind of fuel, the $O_2$ concentration calculation part 52 may be configured to select a [conversion coefficient], [EGR correction coefficient] or [catalyst correction coefficient] and calculate an $O_2$ concentration by using the selected [conversion coefficient], [EGR correction coefficient] or [catalyst correction coefficient].

In the $O_2$ concentration calculation function taking an EGR model into consideration, an $O_2$ concentration after conversion of a reaction equation may be calculated using a conversion equation of [$O_2$ concentration]=[Original $O_2$ concentration]−[Conversion coefficient]×[$CO_2$ concentration variation], and the $O_2$ concentration after conversion of the reaction equation may be corrected using the EGR model. Similarly, in the $O_2$ concentration calculation function taking the EGR model into consideration, an $O_2$ concentration after conversion of the reaction equation may be calculated using the conversion equation of [$O_2$ concentration]=[Original $O_2$ concentration]−[Conversion coefficient]×[$CO_2$ concentration variation], and the $O_2$ concentration after conversion of the reaction equation may be corrected using the catalyst model.

Although the $O_2$ concentration calculation part 52 is intended to calculate an $O_2$ concentration from a $CO_2$ concentration in the above embodiment, it may be configured to calculate an $O_2$ concentration by using an $H_2O$ concentration obtained by the individual component analysis part 512 and the combustion reaction equation. In this case, an average $O_2$ concentration may be calculated by, for example, weighting and averaging the $O_2$ concentration obtained from the $CO_2$ concentration and the $O_2$ concentration obtained from the $H_2O$ concentration.

Alternatively an $O_2$ concentration may be calculated by a machine learning device that performs machine learning using, for example, training data including a $CO_2$ concentration measured by an FTIR spectrometer and an $O_2$ concentration measured by an FID meter.

Specifically the machine learning device performs the machine learning by using the training data including a relationship between conservation law of a fuel combustion reaction equation and individual atoms in EGR, a $CO_2$ concentration measured by the FTIR spectrometer and an $O_2$ concentration measured by the FID meter.

The training data may include concentrations of $H_2O$, CO, NO, $NO_2$, and $N_2O$ measured by the FTIR spectrometer, an EGR rate obtained by the EGR meter, and circumferential situations such as measurement conditions. Examples of the circumferential situations include values related to physical attributes such as a temperature and pressures of a measurement sample, engine combustion information (information about supercharging, EGR, rich stoichiometry/lean, laminar flow, uniform flow, direct injection and port injection), engine head shape, ignition timing, catalyst structure, oxygen content in fuel, inorganic gas component, Soot concentration, SOF concentration, engine type, engine rotation speed, load information, hot start, cold start, catalyst temperature and gear ratio. A correlation expressed by a machine learning model may employ, as a parameter, part or all of these circumferential situations. Only circumferential situations that strongly affect (namely, have high a relationship with) an $O_2$ concentration obtained by the $O_2$ meter.

Figure 5:
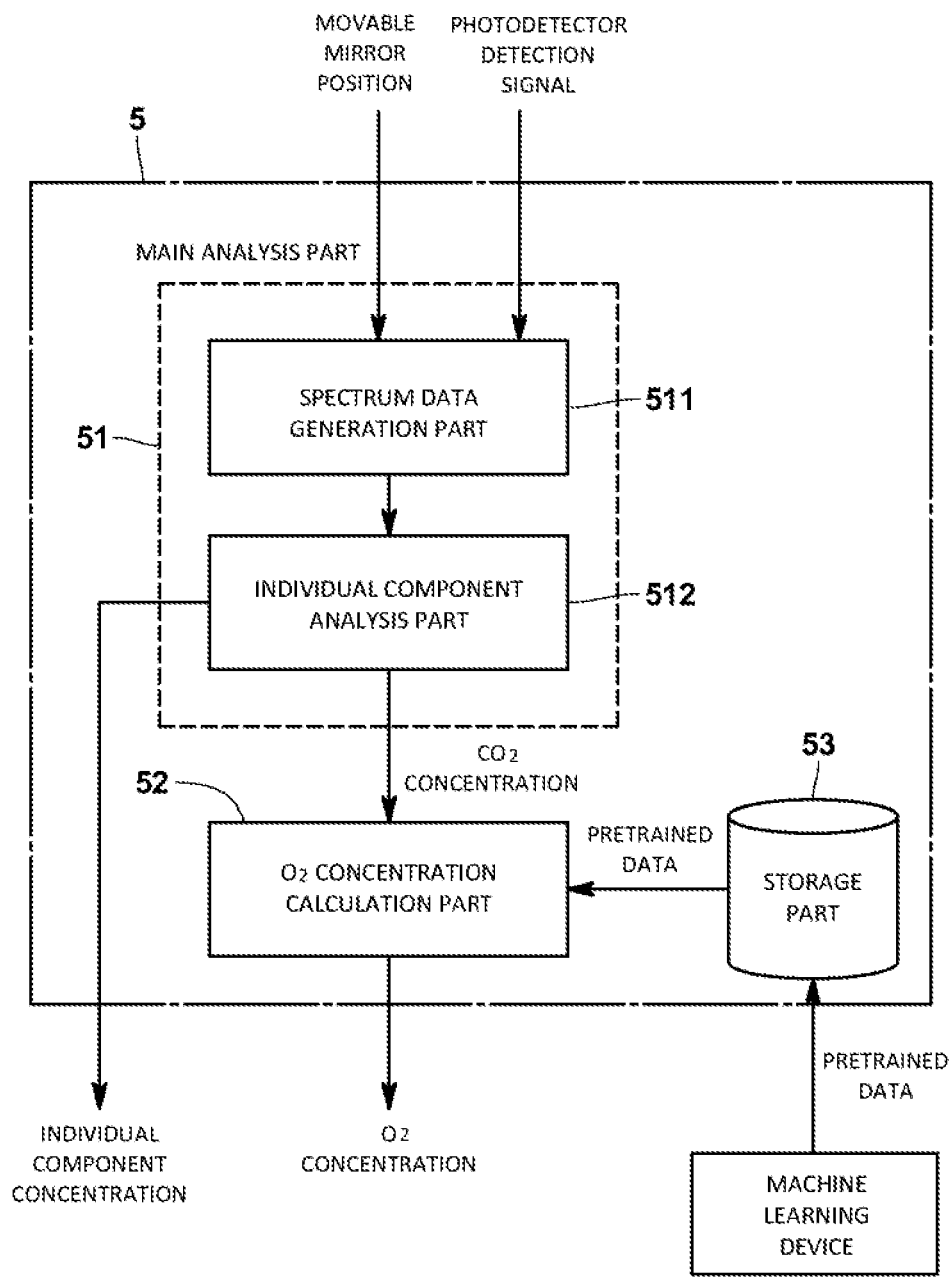
FIG. 5 is a functional block diagram of an arithmetic processing part in a modified embodiment.

As illustrated in FIG. 5, the arithmetic processing part 5 of the exhaust as analyzer 100 includes the storage part 53 to store pretrained data obtained by the machine learning device. The $O_2$ concentration calculation part 52 calculates an $O_2$ concentration by using, for example, the pretrained data and a $CO_2$ concentration obtained by the $CO_2$ concentration calculation part (individual component analysis part 512).

Alternatively, the $O_2$ concentration calculation part 52 of the exhaust gas analyzer 100 may be configured to calculate an $O_2$ concentration in exhaust gas by using the combustion reaction equation and a value indicating an oxygen desorption or absorption amount by the catalyst, instead of using an EGR rate or a value related to the EGR rate.

Although the $O_2$ concentration calculation part 52 in the above embodiment calculates an $O_2$ concentration in exhaust gas assuming that fuel is completely burned, the $O_2$ concentration calculation part 52 may be configured to calculate an $O_2$ concentration assuming that fuel is incompletely burned.

Although the exhaust gas measurement system 200 in the above embodiment is intended for use in testing a completed vehicle V by using the chassis dynamometer, it may be intended for use in testing engine performance by using, for example, an engine dynamometer, or in testing power train performance by using a dynamometer.

Although the exhaust gas analyzer in the above embodiment is configured to employ the FTIR method, it may employ other analysis method using infrared light, such as non-dispersive infrared absorption (NDIR) method.

Besides the above, various modifications and combinations of the embodiments may be made without departing from the spirit and scope of the present invention.

DESCRIPTION OF THE REFERENCE NUMERAL 100 exhaust gas analyzer
1 infrared light source
4 photodetector
512 individual component analysis part ($CO_2$ concentration calculation part)
52 $O_2$ concentration calculation part

What is claimed is:

1. An exhaust gas analyzer to analyze exhaust gas discharged from an internal combustion engine, comprising:
   an infrared light source to irradiate infrared light to the exhaust gas;
   a photodetector to detect the infrared light after passing through the exhaust gas;
   a processor configured to calculate a $CO_2$ concentration in the exhaust gas on a basis of a detection signal obtained by the photodetector, and to calculate an $O_2$ concentration in the exhaust gas from the $CO_2$ concentration by using a fuel combustion reaction equation and an EGR rate in an exhaust gas recirculation system or a value related to the EGR rate such that the exhaust gas analyzer measures the $O_2$ concentration that does not absorb the infrared light, wherein the fuel combustion reaction equation indicates a relationship between $CO_2$ and $H_2O$ generated during fuel combustion; and
   a catalyst disposed in an exhaust pipe connecting to the internal combustion engine so as to analyze exhaust gas after passing through the catalyst, wherein
   the processor further calculates the $O_2$ concentration in the exhaust gas by using a value indicating an oxygen desorption amount or oxygen absorption amount by the catalyst, a conversion coefficient obtained from a ratio of an $O_2$ coefficient and a $CO_2$ coefficient in the fuel combustion reaction equation, an EGR correction coefficient obtained from the EGR rate or a value related to the EGR rate, a catalyst correction coefficient obtained from a value indicating an oxygen desorption amount or oxygen absorption amount by the catalyst, and a $CO_2$ concentration variation calculated by the processor.

2. The exhaust gas analyzer according to claim 1, wherein the processor calculates the $O_2$ concentration according to a following equation:

$$[O_2\text{ concentration}] = [\text{Original } O_2\text{ concentration}] - [\text{Conversion coefficient}] \times [\text{EGR correction coefficient}] \times [CO_2 \text{ concentration variation}].$$

3. The exhaust gas analyzer according to claim 1, wherein the processor stores beforehand a relational expression indicating a relationship between the EGR rate or the value related to the EGR rate and the $CO_2$ concentration, and calculates the EGR correction coefficient from the $CO_2$ concentration by using the relational expression.

4. The exhaust gas analyzer according to claim 3, wherein individual parameters of the relational expression are generated from training data comprising a previously acquired EGR rate or a value related to the previously acquired EGR rate and a previously acquired $CO_2$ concentration.

5. The exhaust gas analyzer according to claim 1, wherein the processor calculates the $O_2$ concentration according to a following equation:

$$[O_2\text{ concentration}] = [\text{Original } O_2\text{ concentration}] - [\text{Conversion coefficient}] \times [\text{EGR correction coefficient}] \times [\text{Catalyst correction coefficent}] \times [CO_2 \text{ concentration variation}].$$

6. The exhaust gas analyzer according to claim 1, wherein the processor stores beforehand a relational expression indicating a relationship between a value indicating an oxygen desorption amount or oxygen absorption amount by the catalyst and a $CO_2$ concentration, and calculates from the $CO_2$ concentration a value indicating an oxygen desorption amount or oxygen absorption amount by the catalyst by using the relational expression.

7. The exhaust gas analyzer according to claim 1, wherein the processor calculates the $CO_2$ concentration in the exhaust gas using Fourier transform infrared spectroscopy.

8. An exhaust gas analysis method for analyzing exhaust gas discharged from an internal combustion engine via an exhaust pipe connected to the internal combustion engine and having a catalyst disposed therein, comprising:
   irradiating infrared light to the exhaust gas;
   detecting the infrared light after passing through the exhaust gas;

generating a detection signal on a basis of the detected infrared light;

calculating a carbon dioxide ($CO_2$) concentration in the exhaust gas on a basis of the detection signal; and calculating an oxygen ($O_2$) concentration in the exhaust gas from the $CO_2$ concentration by using a fuel combustion reaction equation, an EGR rate in an exhaust gas recirculation system or a value related to the EGR rate, a value indicating an oxygen desorption amount or oxygen absorption amount by the catalyst, a conversion coefficient obtained from a ratio of an $O_2$ coefficient and a $CO_2$ coefficient in the fuel combustion reaction equation, an EGR correction coefficient obtained from the EGR rate or a value related to the EGR rate, a catalyst correction coefficient obtained from a value indicating an oxygen desorption amount or oxygen absorption amount by the catalyst, and a $CO_2$ concentration variation such that the $O_2$ concentration that does not absorb the infrared light is measured.

9. An exhaust gas analyzer to analyze exhaust gas discharged from an internal combustion engine, comprising:
an infrared light source to irradiate infrared light to the exhaust gas;
a photodetector to detect the infrared light after passing through the exhaust gas; and
a processor to calculate a $CO_2$ concentration in the exhaust gas on a basis of a detection signal obtained by the photodetector, and to calculate an $O_2$ concentration in the exhaust gas from pretrained data generated from training data comprising a $CO_2$ concentration and an $O_2$ concentration in the exhaust gas and expressing a correlation between the $CO_2$ concentration and the $O_2$ concentration in the exhaust gas, and from the $CO_2$ concentration calculated by the processor such that the exhaust gas analyzer measures the $O_2$ concentration that does not absorb the infrared light.

10. An exhaust gas analyzer to analyze exhaust gas discharged from an internal combustion engine, comprising:
an infrared light source to irradiate infrared light to the exhaust gas;
a photodetector to detect the infrared light after passing through the exhaust gas;
a processor to calculate a $CO_2$ concentration in the exhaust gas on a basis of a detection signal obtained by the photodetector, and to calculate an $O_2$ concentration in the exhaust gas from the $CO_2$ concentration by using a fuel combustion reaction equation and an EGR rate in an exhaust gas recirculation system or a value related to the EGR rate such that the exhaust gas analyzer measures the $O_2$ concentration that does not absorb the infrared light, wherein the fuel combustion reaction equation indicates a relationship between $CO_2$ and $H_2O$ generated during fuel combustion; and;
a catalyst disposed in an exhaust pipe connecting to the internal combustion engine so as to analyze exhaust gas after passing through the catalyst, wherein
the processor calculates the $O_2$ concentration in the exhaust gas by using a value indicating an oxygen desorption amount or oxygen absorption amount by the catalyst, a conversion coefficient obtained from a ratio of an $O_2$ coefficient and a $CO_2$ coefficient in the fuel combustion reaction equation, an EGR correction coefficient obtained from the EGR rate or a value related to the EGR rate, a catalyst correction coefficient obtained from a value indicating an oxygen desorption amount or oxygen absorption amount by the catalyst, and a $CO_2$ concentration variation calculated by the processor.

* * * * *